United States Patent [19]

Zabriskie et al.

[11] Patent Number: 4,743,538

[45] Date of Patent: May 10, 1988

[54] TEST FOR RHEUMATIC FEVER AND MONOCLONAL ANTIBODIES USEFUL THEREFOR

[75] Inventors: John B. Zabriskie; Daniel R. Buskirk, both of New York, N.Y.

[73] Assignee: The Rockefeller University, New York, N.Y.

[21] Appl. No.: 724,076

[22] Filed: Apr. 17, 1985

[51] Int. Cl.[4] .................... C07K 15/04; C12N 5/00; G01N 33/554

[52] U.S. Cl. .......................... 435/7; 435/29; 435/68; 435/70; 435/172.2; 435/240.27; 435/810; 436/548; 436/810; 935/104; 935/108; 935/110; 530/387

[58] Field of Search ............. 260/112 R; 530/387; 424/85, 87, 88, 92; 435/7, 29, 68, 70, 172.2, 240, 810; 436/501, 503, 506, 507, 509, 548, 800, 805, 808, 811, 821; 935/104, 108, 110

[56] References Cited

U.S. PATENT DOCUMENTS 4,521,334  6/1985  Beachey ........................... 424/88
4,554,248 11/1985  Green et al. ...................... 435/7

OTHER PUBLICATIONS

Patarroyo, M. E. et al., *Streptococcal Disease and the Immune Response*, Academic Press (1980), pp. 369–375.
Stollerman, G. H. et al., *Rheumatic Fever and Streptoccoal Infection*, N.Y. Greene, (1975), pp. 181–208.
Gibofsky, A. et al., American Heart Association Monograph, No. (114), Abstract 1282, (1985).

*Primary Examiner*—Margaret Moskowitz
*Attorney, Agent, or Firm*—Wyatt, Gerber Shoup and Badie

[57] ABSTRACT

Monoclonal antibodies which react specifically with a complementary rheumatic fever associated antigen on human B-lymphocytes derived from hybridoma cell line HB8783, process for preparing such antibodies, the use of antibodies for detecting rheumatic fever in mammals and test kit containing the antibodies.

7 Claims, No Drawings

TEST FOR RHEUMATIC FEVER AND MONOCLONAL ANTIBODIES USEFUL THEREFOR

BACKGROUND OF THE INVENTION

This invention is concerned with monoclonal antibodies useful to detect humans who are susceptible to attacks of rheumatic fever. It is concerned also with methods of producing and using such antibodies, compositions containing them, hybridoma cell lines useful for producing them and diagnostic kits containing them.

The techniques for producing hybridoma cell lines and monoclonal antibodies utilizing mouse myeloma cells and spleen cells from immunized mice were first described by Kholer and Milstein in *Nature* 256, 495 (1975). Subsequently considerable effort has been expended in the production of new cell lines and monoclonal antibodies. The general techniques applicable to such production are well known and understood. However, knowledge of the procedures is not a guarantee of success. There are many difficulties and unexpected impediments. In fact, there is no assurance, prior to attempting to prepare a given hybridoma, that it will produce antibody if obtained, or that the antibody produced will have the desired specificity. The degree of success depends on the type of antigen employed, the fusion technology applied, and the selectin techniques used for identifing and isolating the hybridoma with the desired specificity which subsequently must be maintained by long term culture technology.

Individuals susceptible to attacks by rheumatic fever presently constitute a large segment of the world population. In India there are an estimated 8 million new cases of rheumatic fever per year, in Mexico there are 3 million cases, and in Africa 10 million. At least 60% of these individuals will ultimately develop serious chronic heart disease.

There is strong evidence to suggest that there is a particular B-cell alloantigen, the occurrence of which is significantly associated with patients who develop rheumatic fever, Patarroyo, Manuel E. et al, *Streptococcal Diseases And The Immune Response*, Academic Press, 1980, page 369. The occurrence of this alloantigen in unaffected, apparently normal individuals, and its inheritance in unaffected family members of patients provides evidence of the genetic nature of the alloantigen.

Briefly, the evidence for the existence of the alloantigen is the fact that a serum, designated serum 883, isolated from a multiparous woman in Bogota, Columbia, correctly identified 70 to 75% of all documented rheumatic fever subjects from different geographical areas of the world.

Rheumatic fever attacks in susceptible individuals are sequelae of streptococcal sore throats. In the present state of the art for preventing rheumatic fever attacks, documented sore throats as evidenced by positive cultures and rise in streptococcal antibody are treated with penicillin for ten days either by mouth or by injection. The reason for this procedure is that failure to heal the streptococcal infection during this period of time may result in rheumatic fever in 3% of the age group (5 to 18 years) at greatest risk.

At the present time there is no procedure for discovering those who are at risk of contracting the disease prior to the actual rheumatic fever attack. Fortunately, after the acute attack, subsequent attacks can be prevented by placing the patient on daily prophylaxis and penicillin. Clearly, it would be a valuable addition to the physician's armamentaruim if they could identify the susceptibles at birth. If the genetic marker present at birth were available from B-cells, a small amount of heparinized cord blood obtained from each newborn could be tested for the presence of the marker. Positive tests would identify the child as rheumatic fever susceptible individual (about 19% of the population). The mother would be notified that her child is at risk of contracting rheumatic fever and all of the child's sore throats would then be treated carefully for ten days, usually with penicillin. Those children who are not susceptible when infected with a streptococcal sore throat might be treated for a lesser period, i.e., 4 to 5 days. The cost savings are readily apparent.

Such identification tests, while important in relatively affluent countries, are of far greater importance in third world countries. In these countries, with their characteristically large and still growing populations, treatment of all streptococcal sore throats is realistically impossible and financially prohibitive. Identification of susceptible individuals at birth or early in childhood would allow health agencies in such countries to concentrate their efforts on those individuals at high risk. Obviously, an inexpensive method of identifying these individuals would be the optimal way to prevent long term chronic heart disease, one of the most unfortunate results of rheumatic fever. At the present time, a very high proportion of the public health budget is expended to treat symtopmatically and to sustain victims of long standing chronic heart disease resulting from rheumatic fever. Prevention is obviously a less expensive procedure.

THE INVENTION

A novel hybridoma has been invented that is capable of producing novel monoclonal antibodies which can be employed to test for individuals at risk of rheumatic fever. One of these hybridomas has successfully indentified a genetic marker on approximately 95% of documented rheumatic fever patients.

For purposes of this description, documented rheumatic fever patients are those afflicted with disease by the revised Jones criteria. Stollerman, G. H., 1975, *Rheumatic Fever And Streptococcal Infection*, New York: Greene, Chapter 8, page 181.

The observation which served as the seed of this invention was the finding that the multiparous human serum 883 referred to above could correctly identify 70 to 75% of documented rheumatic fever victims. These individuals are identified as 883+. B-lymphocytes from these individuals have been employed to produce the novel hybridoma D8/17.

The steps in the production of the hybridoma of this invention are:

1. Utilizing serum 883, identify those documented rheumatic fever patients who are 883+.
2. Isolate B-lymphocytes from 883+ patient.
3. Immunize an animal, preferably a rodent such as a rat or mouse, with the isolated B-lymphocytes.
4. Isolate whole spleen cells including B-cells from the immunized animal.
5. Fuse the isolated spleen cells with myeloma cells from an animal, preferably a rodent such as a rat or mouse.
6. Select from the fused cells those hybridoma cell lines which react positively with B-lymphocytes from rheumatic fever patients irrespective of whether or not they were 883+ or 883− as defined by the original alloantiserum.

7. Clone the hybridoma cells to produce monoclonal antibodies.

The cloned hybridoma may further be subcloned with dilution in accordance with standard techniques.

As will be explained more fully hereinafter, the hybridoma which derived from one 883+ patient is identified as D8/17. It will be clear to those skilled in the art that once hybridoma cell lines producing D8/17 have been identified, those cell lines can be utilized to produce any desired amount of additional cell lines and antibodies. For this purpose they are properly maintained and propagated in culture or in the peritoneal cavities of mice. They may be stored in liquid nitrogen and revitalized when needed.

DETAILED DESCRIPTION OF THE INVENTION

To assist in the understanding of this invention, there follows a description of a procedure by which hybridoma D8/17 was produced.

A number of well documented rheumatic fever patients who had their acute disease 10 to 20 years were tested with the human alloantiserum mentioned above. The serum divided the patients into two groups: 883+ and 883+. It is emphasized that all individuals had been in fact afflicted with rheumatic fever.

One 883+ patient was selected, and a total of 500 ml of heparinized blood was collected in 150 ml increments at timed intervals. The lymphocytes from the blood samples were separated by the method of Winchester et al, J.Exp.Med. 141, 924 (1975).

A Ficoll-Hypaque sugar-lipid mixture was prepared with a bouyant density of 1.077 compared to water. The heparinized blood was carefully layered on the density mixture and the tubes spun at 2500 rpm for 40 minutes. At this density the red cells and leukocytes sediment to the bottom while the T and B cells are trapped in the Ficoll-Hypaque material. The T and B cells were collected, washed three times in phosphate buffered saline and resuspended at a concentration of one million cells per ml.

To remove the T cells, the cellular suspension was mixed with a 5% suspension of neuraminidase-treated sheep red blood cells, centrifuged at 1000 rpm for 10 minutes and left standing at 4° C. for one hour. The rosetted cells, i.e., cells binding to the sheep red blood cells, and the non-rosetted cells were resuspended in 2-3 ml of Ficoll-Hypaque material at the same bouyant density. The centrifugation was repeated as before. The rosetted T cells sediment to the bottom of the tube leaving a population of B cells, approximately 20% of the cells in the layer not rosetted in the Ficoll-Hypaque mixture. These B cells, which also contained macrophages but less than 2% T-cells, were recovered from the mixture and washed with phosphate buffered saline to prepare them for injection. A 150 ml sample of whole blood yields about 40 million B cells.

To raise antibodies to these human B cells, the cells were injected into mice to immunize them. The cells were divided into two 20-million aliquots and each mouse (two) received a single intraperitoneal injection followed by the injection of 0.2 ml alum (4 mg/ml) as an adjuvant to stimulate the mouse's immune response. Four weeks later a second 20 million B cells were injected into the same mice without adjuvant. Four days later the mice were sacrificed.

The spleens were aseptically removed from the immunized mice and minced with 20 gauge hypodermic needles. The resulting suspension of cells and tissue fragments was pushed through a sterile stainless steel screen. The cell suspension was then washed with serum-free DMEM and centrifuged for 5 minutes at 1000 rpm in a clinical centrifuge. The pellet was suspended in 5 ml of 0.17M ammonium chloried and the suspension kept on ice for 10 minutes with occasional agitation. At the end of 10 minutes, serum-free DMEM was added to bring the total volume back to 50 ml and the cells once again centrifuged for 10 minutes at 1000 rpm.

$P_3U$ myeloma cells growing in log phase were harvested by pelleting in a 50 ml centrifuge tube for 5 minutes at 1000 rpm. The resulting pellet was resuspended in 10ml serum-free DMEM, and, after resuspension was complete, the volume in the tube was brought to 50 ml with serum-free DMEM. The myeloma cells were pelletted in a clinical centrifuge as before, and the resulting pellet was resuspended in 10 ml serum-free DMEM and counted. The spleen cells and the myeloma cells were mixed in a 1:1 ratio.

The spleen cell/myeloma mixture was pelletted for 5 minutes at 1000 rm, and care was taken to remove virtually all the supernatant. The pellet was then suspended in 1.0 ml DMEM containing 40% polyethylene glycol (3200-3700 molecular weight) and 5.6% dimethylsulfoxide, at 37° C. The tube was placed on a vial rotator and rotated at 20 rpm for precisely one minute. At the end of the first minute, an additional 1.0 ml serum-free DMEM at 37° C. was added, and the tube returned to the rotator for 2 minutes. At the end of 2 minutes, 2.0 ml serum-free DMEM was added, once again doubling the volume of the cell suspension. The tube was returned to the rotator for 2 minutes. At the end of 2 minutes, 4.0 ml of DMEM containing 10% horse serum was added to the mixture, which was once again returned to the rotator, this time for 3 minutes. At the end of 3 minutes, 8.0 ml of DMEM/10% horse serum was added to the mixture and returned to the rotator for three minutes, following which the total volume in the tube was brought to 50 ml with DMEM/10% horse serum. The cell mixture was then centrifuged for 5 minutes at 100 rpm. The pellet was resuspended in 10 ml DMEM containing 10% horse serum and supplementary hypoxanthine and thymidine. The total volume was brought to 50 ml and the mixture aliquoted into tissue culture dishes and incubated overnight at 37° C. in an atmosphere of 7% $DO_2$.

The following day an equal volume of DMEM containing 10% horse serum, supplementary hypoxanthine and thymidine and 2X concentration of aminopterin was added to each tissue culture dish, and the cells returned to the incubator. Within a few days hybridoma clones appear, and within a week screening for antibody-producing cells may begin.

The cultures were allowed to grow for about two weeks and then the supernatant was tested for the presence of monoclonal antibody specific for an antigen on the B-cell of rheumatic fever patients.

To conduct the test known as the indirect immunofluorescence technique, an aliquot of the B cells prepared as described above is adjusted so that samples each containing approximately 100,000 cells per 100 ul are placed in microtiter wells, centrifuged at 500×5 for 8 minutes, the supernatant removed by suction and resuspended in 100 ul of cold (4° C.) phosphate buffered saline (PBS) pH 7.2, 1% BSA and 0.02% sodium azide. The cells are centrifuged again at the same speed, with removal of the supernatant. 20 ul of the supernatant under test is added to the suspension, the plate is tapped gently to permit dispersion of the cells in the supernatant under test and the plate incubated 1hr at 4° C. The plate is then filled with 150 ul of the above solution, centrifuged 500×g for 10 minutes and the supernatant removed. The cells in the plate are washed with the above PBS solution following the last wash and centrifugation, the wash buffer is removed and 20 ul of a fluorescein conjugated goat anti-mouse immunoglobulin is added to the cells and the incubation again occurs for 1 hr at 4° C. Following the incubation, the cells are again suspended in 150 ul of the cold PBS solution, centrifuged and supernatant fluid removed. The cells are gently resuspended in 20 ul of PBS solution and placed on glass slides and coverslips added. The fluorescing cells are read using a standard fluorescent microscope. Results are read as positive when 60% of the B cell population are seen to be fluorescing.

For confirmation of the above results a standard cytotoxicity assay was also employed. The same B cells described above each containing 1000 cells, were placed in wells of Terasaki plates. Each sample was mixed with 2 to 5 ul of the supernatant under test. A known amount of complement was added (usually fresh guinea pig complement) and then a small amount of Trypan blue dye.

In this standard test, those antibodies which are positive will react with an antigen on a B cell of a rheumatic fever patient. In the presence of complement from any source, e.g. of giunea pig serum, the antibody is cytotoxic to the cell and permits penetrance of the dye into the cell. Thus positive cells turn blue and can be easily detected under the microscope. If 80% or more of the test cells turn blue the test is read as positive and indicates the presence of a specific antigen on the cell surface of the B cell.

Over one hundred supernatants were tested in this manner and hybridoma D8/17 was found to be specific for all rheumatic individuals originally designated either as 883+ or 883− by human alloantiserum 883.

Thus 95% of all rheumatic fever patients exhibit an antigen on their B cells if the single hybridoma clone of this invention is used for testing.

The monoclonal antibody of this invention obtained from DR8/17 does not react with any of the antigens on a selected panel of lymphocytes. The lymphocytes covering the A, B, C and DR-1 through DR-8 as well as HLA specificities were selected because all human beings have certain of these genetically determined alloantigens on the surface of their lymphocytes irrespective of whether or not they are susceptible to rheumatic fever. The fact that the antibody does not react with any antigens on these lymphocytes provides additional evidence for the specificity of the antibody for antigens unique to rheumatic fever susceptible individuals.

The procedures described above produce the novel hybridoma which, in turn, produces the novel monoclonal antibody of this invention. The antibody can be isolated by standard procedures, but it is not necessary to do so. Typically useful procedures include, for example, precipitation, dialysis, chromatography, membrane filtration and electrophoresis.

One such procedure which was employed to isolate the antibody was to precipitate the antibody out of supernatant fluid of the growing culture with ammonium sulfate. In this procedure 100 ml of supernatant fluid from an actively growing hybridoma antibody secreting clone was slowly mixed at 27° C. with 24.2 g of ammonium sulfate to make a 40% solution of ammonium sulfate in the supernatant material. The mixture was allowed to stand for 30 minutes under gentle agitation with a magnetic stirring bar. The supernatant was discarded and the pellet was washed 3 times in a 40% solution of ammonium sulfate with centrifugation at 10,000 RPM each time. Finally, the pellet was resuspended in 2 to 5 ml phosphate buffered saline containing 0.02% sodium azide and passed over a 30 ml DEAE cellulose column equilibrated with the same buffer. The fall-through peak contained the purified antibody which was then concentrated to 2 to 3 ml and stored in ½ ml aliquots until use.

An alternative method is to absorb the monoclonal antibody on an antiserum raised to mouse immunoglobulin. For example, the antiserum may be coupled to cyanogen bromide activated Sepharose beads. The supernatant fluid containing the monoclonal antibody is passed over the column thereby trapping it on the column. After thorough washing of the column with a phosphate buffered solution pH 7.6, the next step is to pass a low pH buffer (sodium citrate pH 2.5–3.0) which dissociates the monoclonal antibody. The dissociated antibody is collected from the eluate of the column, neutralized to pH 7.6 with 0.1 N sodium hydroxide solution and concentrated for further use.

The processes of this invention permit the preparation of a hybridoma which secretes a monoclonal antibody into a culture medium. The supernatants of the culture medium will contain the monoclonal antibody in sufficient concentration so that the supernatant can be used for almost any purpose as though it were a monoclonal antibody. The hybridoma culture can be employed in accordance with standard procedures with any of a number of known and readily available culture mediums to prepare additional hybridomas and antibodies.

While BALB/c mice are the presently preferred subjects for immunization, it is recognized that other mouse strains may be employed, and that other rodents, particularly rats, may also be used.

The presently used mouse myeloma $P_3u$ cells arose from a fusion between BALB/c spleen cells and BALB/c myeloma cells producing a cell line lacking immunoglobulin syntheses and secretion. However, many other mouse myeloma cell lines are known and available, for example from deposit banks. These can be utilized in the practice of this invention. The cell line should preferably be of the drug resistant type illustrated above so that unfused myeloma cells will not survive. The most common class are the 8-azaguanine resistant cell lines which lack the enzyme HGPRT and therefore will not multiply in HAT medium. The myeloma cell lines are also preferred to be of the immunoglobulin non-secreting kind, e.g. the $P_3u$ line, so as to avoid contamination of the monoclonal antibody by antibodies produced by the cell. A suitable ratio of spleen cells to myeloma cells for the fusion process is from about 5:1 to 1:05. The preferred ratio is 1:1.

While the presently preferred fusion promotor is PEG (polyethylene glycol) with an average molecular weight of from about 1000 to 4000, other fusion promotors are known and can be used.

The monoclonal antibodies of this invention can be produced from the hybridoma cell line which has been deposited at the American Type Culture Collection and assigned the accession number HB8783. The cell line can be utilized to produce additional antibody in either of two ways.

The purest monoclonal antibody is produced by in vitro cultures of the selected hybridoma in a suitable medium for a suitable period of time. The antibodies may be recovered from the supernatant if desired, but it is not necessary to do so. Suitable mediums and suitable lengths of culturing time are known or may be readily determined. Typical of the several mediums which can be employed are Dulbecco's modified Eagle's medium and RPMI 1640, available from MA Bioproducts, Walkersville, Md.

This in vitro technique produces essentially monospecific monoclonal antibody, essentially free from other antibodies. However, this in vitro method may not produce a sufficient quantity or concentration of antibody for some purposes, since the concentration of monoclonal antibody produced is only about 1-20 ug/ml.

To produce a much greater concentration of slightly less pure monoclonal antibody, the selected hybridoma may be injected intraperitoneally into mice, preferably syngeneic or semi-syngeneic mice. The hybridoma will cause formation of antibody producing tumors in the mice after a suitable incubation time, which will result in high concentration of the desired antibody (about 5-20 mg/ml) in the blood stream and peritoneal exudate (ascites) of the host mouse. Although the host mice also have normal antibodies in their blood and ascites, the concentration of these normal antibodies is only about 5% of the monoclonal antibody concentration. Moreover, since these normal antibodies are not anti-human B-cell in their specificity, the monoclonal antibody obtained from the harvested ascites or from the serum is esentially free of contaminating antibodies.

The monoclonal antibody compositions of this invention are distinguished from antibody compositions normally available, such as human antisera. These latter compositions, even in highly purified form, contain significant amounts of contaminating antibodies. In contrast, the compositions of this invention are essentially free of contaminating antibodies. They therefore lend themselves readily to a number of medical utilities, as will be readily apparent to those skilled in the art. The compositions comprise the antibodies in a medically inert medium, that is a medium which is not toxic and does not adversely affect the physiological activity of the antibody in the selected use. The medium for many uses will be the supernatant of the culture medium in which the hybridoma grows and produces the antibody. It may also be an aqueous medium, e.g., isotonic saline or glucose solution or an oil such as peanut or sesame oil.

One of the most important medical uses for the products of this invention is to detect individuals at risk of rheumatic fever. For this diagnostic purpose, the selected antibody will react with B-lymphocytes from the individual under test to produce, in the case of positive individuals, a detectable product. The B-lymphocytes of positive individuals will be characterized by an antigen reactive with the antibody from D8/17. An antibody containing composition used in any test must contain sufficient antibody to react with the antigen to produce a detectable product. Such diagnostically effective amounts of antibody will vary appreciably with a number of factors well known to those skilled in the art. These include, for example, the sensitivity of the test employed, the instrumentation available and the amount of sample under test.

Any of a large number of clinical tests may be employed utilizing the hybridoma and antibodies of this invention. Typical tests include radioimmunoassay, enzyme linked immunoassay, precipitation, agglutination, direct and indirect immunofluorescence, and complement fixation. These tests may employ competitive and sandwich type assays. The tests may employ detectable labels. The antigen, the monoclonal antibody, or antiantibody such as rabbit anti-mouse serum may be labeled. Useful labels include fluorescent labels such as fluorescein, rhodamine or auramine. Radiosotopes such as $^{14}C$, $131_I$, $125_I$ and $25_S$ may be employed. Enzyme labels which may be utilized include, for example, $\beta$-glucamidase, $\beta$-D-glucosidase, $\beta$-D-galactosidase, unrease, glucose oxidase plus peroxidase, and acid or alkaline phosphatase. Methods for labeling biological products such as cells, antibodies, antigens and antisera are well known and need not be described.

There are several currently available procedures for detecting these labels including, for example colorimetric, spectrophotometric, fluorospectrophotometric, photometric and gasometric techniques, as well as various instrumental methods of detecting isotopes.

All of the tests which may be usefully employed in accordance with this invention involve the formation of a detectable reaction product which includes a monoclonal antibody of the invention and an antigen which occurs on the B-lymphocytes of persons at risk of rheumatic fever. Of course there may be other components such as an antiantibody in the detectable reaction product.

The presently preferred diagnostic test is the test described above which was employed to recognize the hybridoma of the invention. For diagnostic purposes, the test is used with the hybridoma to recognize the antigen on the B-lymphocytes of persons at risk of rheumatic fever. In the test, 1 ul of the hybridoma is mixed with 1 ul of the B-cell lymphocyte population (2000 cells) from the individual under test, together with 5 ul of rabbit complement and a dye such as trypan blue or Eosin (2.5% aqueous solution) and 5 ul of formalin, pH 7.0. A positive test is indicated by the appearance of a blue or red color which is visible to the naked eye. The color appears because the reaction product of the antibody and the B-lymphocyte antigen is cytotoxic to the lymphocyte in the presence of complement. The cytotoxicity results in rupture of the cell membrane and the dye reacts with a component of the ruptured cell to produce the color.

This procedure is especially useful in situations where sophisticated instrumentation is not available. A low powered simple microscope is all that is required by way of instrumentation for this test. The technician need not be highly trained. A typical kit used to perform the test will contain a diagnostic quantity of the antibody of this invention together with complement and the dye. The presently preferred complement is guinea pig complement, but others may be employed.

In another test which is applicable when suitable instrumentation is available, blood from the individual under test is incubated at about 20° to 45° C. in a buffer such as phosphate buffered saline at pH 7.2 to 7.6 with a mixture containing a monoclonal antibody of the invention in labeled form. If there is a positive reaction, the reaction product of the antigen-labeled antibody can be detected using an instrument adapted to the selected label.

A kit for this test would contain buffer and a diagnostic amount of a labeled monoclonal antibody of the invention.

The sensitivity of this test can be improved by utilizing the antiantibody as a so-called marker antibody. In this procedure, the blood from the individual under test is incubated in the buffer at the selected temperature with a mixture containing a monoclonal antibody of this invention and a labeled antiserum such as goat or rabbit antimouse antibody conjugated with fluorescein. The detectable product formed in a positive test is the reaction product of the B-lymphocyte antigen, a monoclonal antibody and the labeled antiserum. The product, if labeled with fluorescein, can be detected with a fluorometer. Any other labels known in the art and not destroying the antibody reactivity can be used to enhance the detectability of the antigen. Such labels are, for example, radioisotopes, e.g. $^{125}I$, $^{131}I$, $^{3}H$ or $^{14}C$ (RIA), or enzymes, e.g. horseradish peroxidase, alkaline phosphatase $\beta$-D-galactosidase and the like (ELISA).

What is claimed is:

1. A monoclonal antibody derived from hybridoma cell line HB8783 or a subclone thereof which reacts specifically with the complementary rheumatic fever associated antigen on human B-lymphocytes, but not with known HLA antigens of the A, B, C, DR-1 through DR-8 loci on human B-lymphocytes.

2. A composition comprising hybridoma cell line HB8783 or a subclone thereof and a culture medium therefore.

3. A process for preparing a monoclonal antibody which reacts specifically with the complementary rheumatic fever associated antigen on human B-lymphocytes, but not with known HLA antigens of the A, B, C, DR-1 through DR-8 loci on human B-lymphocytes which comprises culturing hybridoma cell lines HB8783 or a subclone thereof in a culture medium therefore and recovering the antibody from the supernatant of the culture medium.

4. A method of detecting a human at risk of rheumatic fever which comprises reacting B-lymphocytes from said individual with a composition containing a diagnostically effective amount of a monoclonal antibody derived from hybridoma cell lines HB8783 or a subclone thereof and, in the case of a positive test, detecting the presence of a reaction product containing said monoclonal antibody and the complementary antigen from the B-lymphocytes, said antibody being characterized as reacting specifically with the complementary rheumatic fever associated antigen on human B-lymphocytes, but not with known HLA antigens of the A, B, C, DR-1 through DR-8 loci on human B-lymphocytes.

5. A monoclonal antibody composition containing a diagnostically effective amount of the monoclonal antibody derived from hybridoma cell line HB8783 or a subclone thereof and substantially free of contaminating antibodies, said antibody being characterized as reacting specifically with the complementary rheumatic fever associated antigen on human B-lymphocyte cells, but not with known HLA antigens of the A, B, C, Dr-1 through DR-8 loci human B-lymphocytes.

6. A test kit for detecting a human at risk of rheumatic fever comprised of a container which contains:
   a. A sufficient amount of a monoclonal antibody derived from hybridoma cell lines HB8783 or a subclone thereof to react specifically with the complementary rheumatic fever associated antigen on human B-lymphocytes, but not with known HLA antigens of the A, B, C, Dr-1 through DR-8, loci on human B-lymphocytes,
   b. A sufficient amount of a second antibody to react with said monoclonal antibody to produce a detectable product.

7. A test kit for determining a human at risk of rheumatic fever comprised of a container which contains:
   a. A sufficient amount of a monoclonal antibody derived from hybridoma cell lines HB 8783 or a subclone thereof to react specifically with the complementary rheumatic fever associated antigen on human B-lymphocytes, but not with known HLA antigens of the A, B, C, DR-1 through DR-8 loci on human B-lymphocytes and lyse said B-lymphocytes in the present of complement,
   b. A sufficient amount of a dye which will visualize said lysed B-lymphocytes in the present of an amount of complement effective to lyse said B-lymphocytes, and
   c. An effective amount of complement.

* * * * *